(12) United States Patent
Palmerton et al.

(10) Patent No.: US 10,398,452 B2
(45) Date of Patent: Sep. 3, 2019

(54) METHOD AND SYSTEM FOR VACUUM SUCTION

(71) Applicant: Buffalo Filter LLC, Lancaster, NY (US)

(72) Inventors: Christopher A. Palmerton, Clarence, NY (US); Samantha Bonano, Williamsville, NY (US); Daniel R. Palmerton, Elma, NY (US); Gregory Pepe, Lancaster, NY (US); Anthony Lizauckas, III, Williamsville, NY (US); Kyrylo Shvetsov, Depew, NY (US)

(73) Assignee: BUFFALO FILTER, LLC, Lancaster, NY (US)

(*) Notice: Subject to any disclaimer, the term of this patent is extended or adjusted under 35 U.S.C. 154(b) by 363 days.

(21) Appl. No.: 14/901,235

(22) PCT Filed: Jun. 26, 2014

(86) PCT No.: PCT/US2014/044394
§ 371 (c)(1),
(2) Date: Dec. 28, 2015

(87) PCT Pub. No.: WO2014/210350
PCT Pub. Date: Dec. 31, 2014

(65) Prior Publication Data
US 2016/0367266 A1    Dec. 22, 2016

Related U.S. Application Data

(60) Provisional application No. 61/839,581, filed on Jun. 26, 2013.

(51) Int. Cl.
*A61B 17/16* (2006.01)
*G06F 19/00* (2018.01)
(Continued)

(52) U.S. Cl.
CPC ...... *A61B 17/1626* (2013.01); *A61B 17/0469* (2013.01); *A61B 17/0482* (2013.01);
(Continued)

(58) Field of Classification Search
CPC ....... A61B 17/14; A61B 17/141; A61B 17/16; A61B 17/1622; A61B 17/1626; G06F 19/327
See application file for complete search history.

(56) References Cited

U.S. PATENT DOCUMENTS

| | | |
|---|---|---|
| 5,451,222 A | 9/1995 | De Maagd et al. |
| 6,379,149 B1* | 4/2002 | Franetzki ............. A61C 1/0038 433/114 |

(Continued)

OTHER PUBLICATIONS

The International Search Report and Written Opinion of the searching authority for the PCT Application Application Serial No. PCT/US2014/044394; dated Oct. 30, 2014.

*Primary Examiner* — Christopher J Beccia
(74) *Attorney, Agent, or Firm* — William R. Zimmerli

(57) ABSTRACT

A powered surgical device for cutting or drilling having a mechanical cutting or drilling assembly, a fluid inlet, and a vacuum source port for connecting to a vacuum source. The vacuum source port is disposed in fluid communication with the fluid inlet. The surgical device is configured and arranged to cause an aerosol generated by the mechanical cutting or drilling assembly to be suctioned into the fluid inlet when the vacuum source port is connected to a vacuum source.

16 Claims, 2 Drawing Sheets

(51) Int. Cl.
*A61B 90/30* (2016.01)
*A61B 90/98* (2016.01)
*G16H 40/20* (2018.01)
*A61B 17/04* (2006.01)
*A61B 17/06* (2006.01)
*A61B 17/062* (2006.01)
*A61B 17/00* (2006.01)
*A61B 17/29* (2006.01)
*A61B 90/00* (2016.01)

(52) U.S. Cl.
CPC .... *A61B 17/0625* (2013.01); *A61B 17/06133* (2013.01); *A61B 17/1622* (2013.01); *A61B 90/30* (2016.02); *A61B 90/98* (2016.02); *G16H 40/20* (2018.01); *A61B 2017/0023* (2013.01); *A61B 2017/00221* (2013.01); *A61B 2017/00367* (2013.01); *A61B 2017/00473* (2013.01); *A61B 2017/00477* (2013.01); *A61B 2017/0479* (2013.01); *A61B 2017/2927* (2013.01); *A61B 2090/0811* (2016.02); *A61B 2217/005* (2013.01); *A61B 2218/008* (2013.01)

(56) References Cited

U.S. PATENT DOCUMENTS

| | | | |
|---|---|---|---|
| 6,524,307 B1* | 2/2003 | Palmerton | A61B 18/00 604/22 |
| 6,908,455 B2* | 6/2005 | Hajianpour | A61M 1/0039 604/266 |
| 7,204,810 B2 | 4/2007 | Hynes et al. | |
| 8,372,049 B2* | 2/2013 | Jaeb | A61M 1/0088 604/313 |
| 8,915,894 B1* | 12/2014 | Lonky | A61M 37/00 604/289 |
| 2011/0208086 A1* | 8/2011 | Hibner | A61B 10/0275 600/566 |
| 2011/0257614 A1 | 10/2011 | Urich et al. | |
| 2012/0288821 A1 | 11/2012 | Meyer | |
| 2013/0218186 A1* | 8/2013 | Dubois | A61B 17/32002 606/180 |

\* cited by examiner

METHOD AND SYSTEM FOR VACUUM SUCTION

CROSS-REFERENCE TO RELATED APPLICATION

The present invention claims priority benefit of U.S. Provisional Patent Application No. 61/839,851 filed Jun. 26, 2013, entitled "Method and System for Vacuum Suction" which is incorporated herein by reference.

FIELD OF THE INVENTION

The present invention relates generally to vacuum suction and more specifically to methods and systems for vacuum suction for a cutting or drilling device in a medical environment.

BACKGROUND ART

When a surgical tool such as a drill or blade is used to cut through bones, bone tissues or other portions of a body; aerosol, smoke or other particles and fluids may be generated or ejected from the surgical site. The removal of aerosol, smoke, or other particles and fluids from the surgical environment helps to protect the medical personnel and the patient from injury or illness due to contact with these materials during surgical procedures.

BRIEF SUMMARY OF THE INVENTION

With reference to the corresponding parts portions or surfaces of the disclosed embodiment, merely for the purposes of illustration and not by way of limitation, provided is a powered surgical device (100, 200) for cutting or drilling having a mechanical cutting or drilling assembly (120, 220), a fluid inlet (140, 240), and a vacuum source port (160, 260) for connecting to a vacuum source. The vacuum source port is in fluid communication with the fluid inlet. The surgical device is configured and arranged to cause an aerosol generated by the mechanical cutting or drilling assembly to be suctioned into the fluid inlet when the vacuum source port is connected to a vacuum source.

The mechanical cutting or drilling assembly may have a holder for a cutting or drilling element.

The fluid inlet may be arranged adjacent to the cutting or drilling element.

The fluid inlet may be configured and arranged such that when a vacuum source is coupled to the vacuum source port, a fluid suction flow may be created across the cutting or drilling element.

The cutting or drilling element may be a drill bit or a saw blade.

The powered surgical device may further have a vacuum source (260) in fluid communication with the vacuum source port. The vacuum source may be a blower or a pump.

The mechanical cutting or drilling assembly may be a motor. The motor may be an electric rotary motor or reciprocating motor.

The powered surgical device may further have a filter (250) arranged to filter a flow between the inlet and the vacuum source port. The powered surgical device may further have a filter chamber arranged in a fluid flow path between the inlet and the vacuum port. The filter chamber may be configured and arranged to receive a disposable filter (250). The filter chamber has an RFID reader (256) for reading an RFID tag (252) on a disposable filter (250). The filter chamber has an RFID writer (256) for writing filter usage data to a writable RFID tag (252) on a disposable filter.

The powered surgical device may further have a liquid capture system (242) for separating liquids from a flow passing from the inlet towards the vacuum source port. The powered surgical device may further have a liquid exhaust port. The powered surgical device may further have a liquid capture canister (244). The powered surgical device may further have a moisture wick for absorbing moisture from a flow passing from the inlet towards the vacuum source port.

The powered surgical device may further have a control switch (262) for controlling a fluid flow passing from the inlet to the vacuum source port. The control switch may control a vacuum source or a valve. The control switch may be a wirelessly active switch. The wireless control switch may be a radio, wife, Bluetooth, or infrared receiver.

The powered surgical device may further have an illumination source.

The powered surgical device may further have a blower port (234) configured and arranged to blow a fluid towards the mechanical cutting or drilling assembly.

In another aspect, a suction adapter is provided for a powered surgical device (300, 400) for cutting or drilling having an attachment assembly (370) for attachment of the adapter (300, 400) to an aerosol generating medical device (301), a fluid inlet (340, 434), and a vacuum source port (360, 460) for connecting to a vacuum source. The vacuum source port is in fluid communication with the fluid inlet. The adapter device is configured and arranged to cause an aerosol generated by the aerosol generating medical device to be suctioned into the fluid inlet when the vacuum source port is connected to a vacuum source.

The fluid inlet may be arranged adjacent to the cutting or drilling element.

The fluid inlet may be configured and arranged such that when a vacuum source is coupled to the vacuum source port, a fluid suction flow may be created across the cutting or drilling element.

The cutting or drilling element may be a drill bit or a saw blade.

The powered surgical device may further have a vacuum source (260) in fluid communication with the vacuum source port. The vacuum source may be a blower or a pump.

The mechanical cutting or drilling assembly may be a motor. The motor may be an electric rotary motor or reciprocating motor.

The suction adapter may further have a filter (250) arranged to filter a flow between the inlet and the vacuum source port. The suction adapter may further have a filter chamber arranged in a fluid flow path between the inlet and the vacuum port. The filter chamber may be configured and arranged to receive a disposable filter (250). The filter chamber has an RFID reader (256) for reading an RFID tag (252) on a disposable filter (250). The filter chamber has an RFID writer (256) for writing filter usage data to a writable RFID tag (252) on a disposable filter.

The suction adapter may further have a liquid capture system (242) for separating liquids from a flow passing from the inlet towards the vacuum source port. The suction adapter may further have a liquid exhaust port. The suction adapter may further have a liquid capture canister (244). The suction adapter may further have a moisture wick for absorbing moisture from a flow passing from the inlet towards the vacuum source port.

The suction adapter may further have a control switch (262) for controlling a fluid flow passing from the inlet to the vacuum source port. The control switch may control a vacuum source or a valve. The control switch may be a wirelessly active switch. The wireless control switch may be a radio, wifi, Bluetooth, or infrared receiver.

The suction adapter may further have an illumination source.

The suction adapter may further have a blower port (234) configured and arranged to blow a fluid towards the mechanical cutting or drilling assembly.

DETAILED DESCRIPTION

Figure 1:
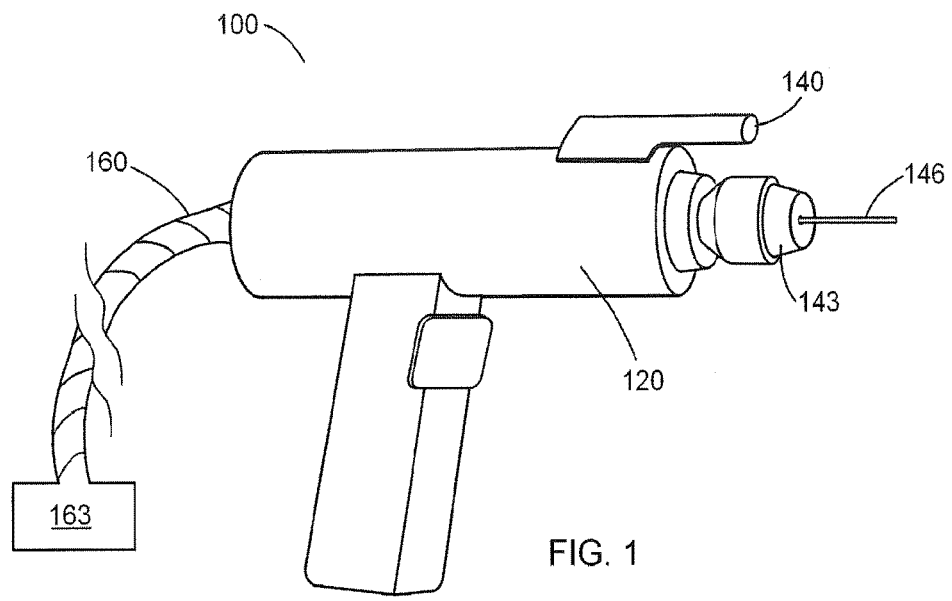
FIG. 1 is a perspective view of a first embodiment surgical device.

At the outset, it should be clearly understood that like reference numerals are intended to identify the same structural elements, portions or surfaces consistently throughout the several drawing figures, as such elements, portions or surfaces may be further described or explained by the entire written specification, of which this detailed description is an integral part. Unless otherwise indicated, the drawings are intended to be read (e.g., crosshatching, arrangement of parts, proportion, degree, etc.) together with the specification, and are to be considered a portion of the entire written description of this invention. As used in the following description, the terms "horizontal", "vertical", "left", "right", "up" and "down", as well as adjectival and adverbial derivatives thereof (e.g., "horizontally", "rightwardly", "upwardly", etc.), simply refer to the orientation of the illustrated structure as the particular drawing figure faces the reader. Similarly, the terms "inwardly" and "outwardly" generally refer to the orientation of a surface relative to its axis of elongation, or axis of rotation, as appropriate.

Referring now to the drawings, FIG. 1 discloses first embodiment 100 of a surgical device system and method of vacuum suction for a device with a mechanical cutting or drilling assembly. System 100 broadly provides a surgical cutting or drilling device which has a vacuum suction assembly capable of suctioning generated aerosols. More specifically, system 100 has the major parts of aerosol generating mechanical cutting/drilling assembly 120, intake/capture port 140, and vacuum source port 160 leading to a vacuum source 163. The vacuum source 163 may comprise a blower or a pump.

Aerosol generating mechanical cutting/drilling assembly contains a motor, a mechanical linkage, a tool holder 143 and a cutting or drilling element/surgical tool 146. Vacuum source port 160 is configured an arranged to be coupled to a vacuum source and intake capture port 140. Intake capture port 140 is configured an arranged to cause an aerosol generated by cutting/drilling assembly 120 to be drawn into capture port 140.

Figure 2:
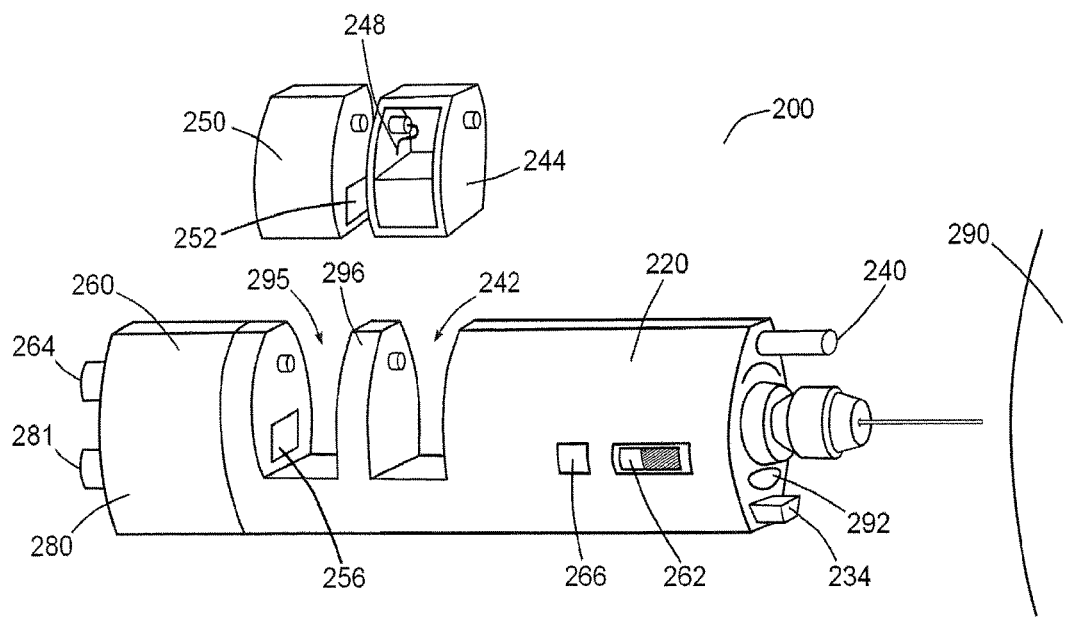
FIG. 2 is a partially exploded perspective view of a second embodiment surgical device.

FIG. 2 shows a second embodiment surgical device system and method of vacuum suction for a device with a mechanical cutting or drilling assembly. System 200 broadly provides a surgical cutting or drilling device which has a vacuum suction assembly capable of suctioning generated aerosols from the cutting or drilling of body portion 290.

More specifically, system 200 has the major parts of aerosol generating mechanical cutting/drilling assembly 220, intake/capture port 240, and vacuum 260. System 200 also contains the additional major components of liquid capture system 242, disposable filter cartridge 150, and blower 280.

Aerosol generating mechanical cutting/drilling assembly 220 contains a motor, a mechanical linkage, a tool holder 223 and a cutting or drilling element/surgical tool 226. As cutting/drilling assembly 220 cuts and/or drills through body portion 290, aerosols, smoke, and or other particles and fluids may be generated and/or ejected from the surgical site.

As shown in FIG. 2, intake capture port 240 is arranged adjacent to cutting/drilling assembly 220. The liquid capture system 242 may be disposed in a chamber 295 formed in the body of the assembly 220. The chamber 295 may be open on one side and may be divided by a wall 296. Disposable canister 244 is removably attached to the body of the assembly 220 to form liquid capture system 242. The disposable canister 244 may snap fit into position by means of cooperating notches and grooves or the like as will be evident to those of ordinary skill in the art based on this disclosure. Intake capture port 240 is in fluid communication with liquid capture system 242, which is in fluid communication with disposable filter cartridge 250, which is in fluid communication with vacuum source 260, which connects with vacuum outlet 264. Disposable filter cartridge 295 may also be removably attached to the body of the assembly 220 in the chamber 295.

Vacuum 260, when turned on, urges a fluid flow from the surgical site, through intake port 240, through liquid capture system 242. Liquid capture system 242 causes liquids to be diverted into disposable canister 244, while remaining fluid is passed on to disposable filter cartridge 250. In addition to the removal of liquid by gravity, a hydrophilic wick 248 may be disposed in the attachment between the intake capture port 240 and the vacuum outlet 264 for absorbing moisture from a flow passing through the system 200. Disposable filter cartridge 250 captures particles from the fluid passing through it. Remaining fluid is drawn through vacuum 260, which is then passed out of system 200 through vacuum outlet 264.

On/off switch 262 is coupled to vacuum 260 and is capable of turning vacuum 260 on and off. On/off switch 262 has a receiver for receiving and acting on a wireless on/off signal. The receiver within on/off switch 262 may be a radio receiver, an infrared receiver, a Bluetooth receiver, an audio receiver, or any other similar receiver/remote control type.

Disposable filter cartridge 250 has RFID tag 252. System 200 has RFID reader/writer 256 which is configured and arranged to read and write to RFID tag 252. RFID tag 252 contains information describing the filter type and filter usage/lifetime information. RFID reader 256 reads this information. After system 200 usage, RFID reader 256 writes updated filter usage information to RFID tag 252. System 200 may contain a controller for controlling the RFID reader, and for causing the system to take an action when the RFID filter life has expired. The action may be generating an alarm, or turning the vacuum off.

System 200 also contains blower 280, which is coupled to blower port 234 and blower intake 280. Blower port 234 is arranged near cutting/drilling assembly 220, and is configured and arranged to cause a fluid flow towards the cutting and drilling element. The fluid flow out of blower port 234 is configured and arranged to cause aerosols generated by cutting/drilling assembly to be drawn with greater efficacy into intake capture port 240.

System 200 may also contain an illumination source 292 to aid the user in seeing.

Figure 3:
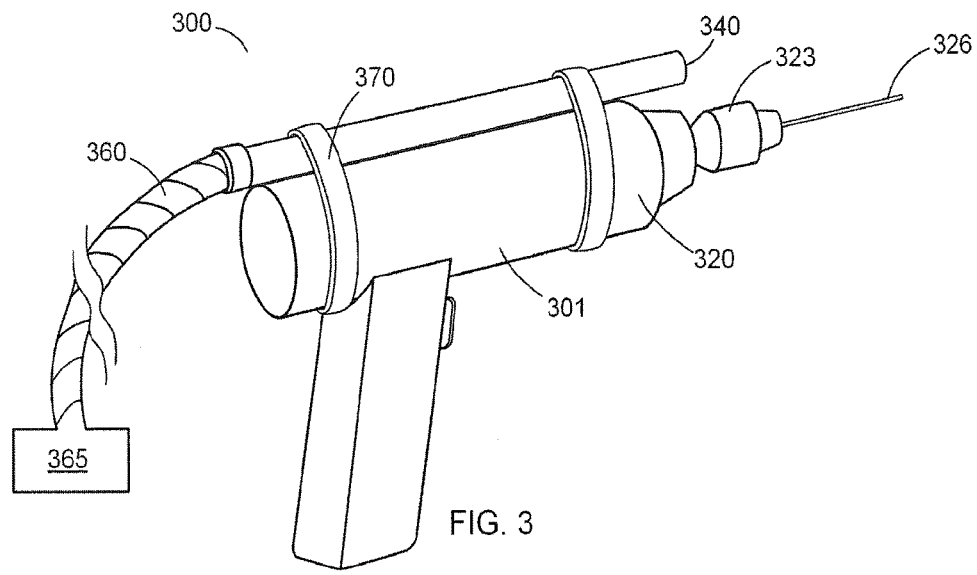
FIG. 3 is a perspective view of a third embodiment surgical device in an adapter configuration.
Figure 4:
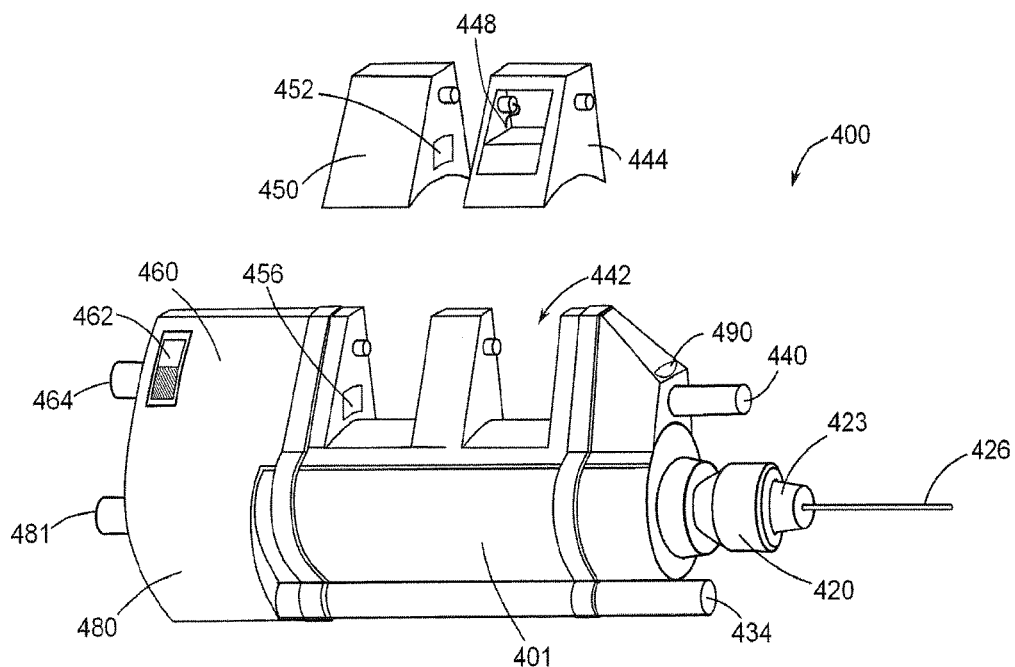
FIG. 4 is a partially exploded perspective view of a fourth embodiment surgical device in an adapter configuration.

FIGS. 3 and 4, are adapter versions of the systems shown in FIGS. 1 and 2. The operation of the systems in FIGS. 3 and 4 are identical to the operation of systems in FIGS. 1 and 2 with the exception that the cutting/drilling assembly is on a device which is physically separate from the adapter system. More specifically, adapters 300 and 400 are configured and arranged to be attached to independent medical devices 301 and 401.

Turning to FIG. 3, device 301 includes a cutting/drilling assembly 320. The aerosol generating surgical tool assembly 320 includes a motor, a mechanical linkage, a tool holder 323 and a surgical tool 326 such as a drill or blade. An intake capture port 340 is disposed in fluid communication with a vacuum outlet 360 that is disposed in fluid communication with a vacuum source 365. The intake capture port 340 and vacuum outlet 360 may be connected and supported by a conduit 369 that is attached to the device 301 by straps 370. The straps 370 may be removable and may have adjustable fasteners such as hook and loop fasteners for attaching around different size devices 301. In addition to the straps 370, other mechanical arrangements for attaching the conduit 369 to the device 301 may also be used included fasteners, adhesives or the like.

In FIG. 4, an attachment 400 for use with a device 401 is shown. Device 401 includes an aerosol generating surgical tool assembly 420 that contains a motor, a mechanical linkage, a tool holder 423 and a surgical tool 426. Intake capture port 440 is arranged adjacent to surgical tool assembly 420. The attachment 400 includes a chamber 495 that may be open on one side and may be divided by a wall 496. Disposable canister 444 is removably attached to the chamber in the body of the attachment 400 to form liquid capture system 442. The canister 444 may be removably attached by means of mechanical engagement such as tongue and groove mating parts or the like as will be evident to those of ordinary skill in the art based on this disclosure. Intake capture port 440 is in fluid communication with liquid capture system 442, which is in fluid communication with disposable filter cartridge 450, which is in fluid communication with vacuum source 460 which connects with vacuum outlet 464. Filter cartridge 450 may also be removably attached to the chamber 495 in the body of the attachment 400.

Vacuum 460, when turned on, urges a fluid flow from the surgical site, through intake port 440, through liquid capture system 442. Liquid capture system 442 causes liquids to be diverted into disposable canister 444, while remaining fluid is passed on to disposable filter cartridge 450. In addition to the removal of liquid by gravity, a hydrophilic wick 448 may be disposed in the attachment between the intake capture port 440 and the vacuum outlet 464 for absorbing moisture from a flow passing through the attachment 400. Disposable filter cartridge 450 captures particles from the fluid passing through it. Remaining fluid is drawing through vacuum 460 which is then passed out of the attachment 400 through vacuum outlet 464.

On/off switch 462 is coupled to vacuum 460 and is capable of turning vacuum 460 on and off. On/off switch 462 has a receiver for receiving and acting on a wireless on/off signal. The receiver within on/off switch 462 may be a radio receiver, an infrared receiver, a Bluetooth receiver, an audio receiver, or any other similar receiver/remote control type.

Disposable filter cartridge 450 has RFID tag 452. Attachment 400 has RFID reader/writer 456 which is configured and arranged to read and write to RFID tag 452. RFID tag 452 contains information describing the filter type and filter usage/lifetime information. RFID reader 456 reads this information. After system 400 usage, RFID reader 456 writes updated filter usage information to RFID tag 452. Attachment 400 may contain a controller for controlling the RFID reader, and for causing the system to take an action when the filter life has expired. The action may include generating an alarm, or turning the vacuum off.

Attachment 400 also includes blower 480 which is coupled to a blower port 434 and blower intake 481. Blower port 434 is arranged near cutting/drilling assembly 420, and is configured and arranged to cause a fluid flow towards the cutting and drilling element/surgical tool 426. The fluid flow out of the blower port 434 is configured and arranged to cause aerosols generated by the cutting/drilling assembly to be drawn with greater efficacy into intake capture port 440. Attachment 400 may also include an illumination source 490 to aid the user in seeing.

The described embodiments resulted in a number of unexpected results and advantages over the prior art. The disclosed embodiments were capable of suctioning a surprisingly substantial portion of the aerosol generated by the cutting/drilling assembly in a surgical environment. The adapter version embodiments allowed these advantages to be applied to a variety of cutting/drilling surgical devices.

Therefore, while the presently-preferred form of the method and system for vacuum suction has been shown and described, and several modifications discussed, persons skilled in this art will readily appreciate that various additional changes may be made without departing from the scope of the invention.

The invention claimed is:

1. A surgical device system, comprising:
   a tool assembly having a body with a distal end, and a proximal end, the tool assembly having a tool holder at the distal end, the tool holder configured for receiving a surgical tool;
   a fluid intake port disposed at the distal end of the tool assembly;
   a blower port disposed at the distal end of the tool assembly;
   a vacuum source disposed in fluid communication with the fluid intake port;
   a blower disposed in fluid communication with the blower port, the blower operable to cause a fluid flow out of the blower port toward the surgical tool and the fluid intake port;
   a liquid capture canister having an inlet and an outlet disposed in fluid communication with the vacuum source and the fluid intake port, the canister configured for removably attaching to the tool assembly; and
   a filter cartridge having an inlet and an outlet disposed in fluid communication with the vacuum source, the fluid intake port, and the liquid capture canister, the filter cartridge configured for removably attaching to the tool assembly, wherein the liquid capture canister is operable to cause liquids to be captured within the liquid capture canister and allows other fluids to pass to the filter cartridge.

2. The surgical device system of claim 1, wherein the surgical tool comprises a drill.

3. The surgical device system of claim 1, wherein the surgical tool comprises a blade.

4. The surgical device system of claim 1, wherein the tool assembly rotates the surgical tool.

5. The surgical device system of claim 1, wherein the tool assembly moves the surgical tool in a reciprocating motion.

6. The surgical device system of claim 1, further comprising an RFID reader disposed on the surgical tool assembly, the RFID reader for reading an RFID tag on the filter cartridge.

7. The surgical device system of claim 1, further comprising an RFID writer disposed on the body of the surgical tool assembly for writing filter usage data to a writeable RFID tag on the disposable filter.

8. The surgical device system of claim 1, further comprising a moisture wick for absorbing moisture from a flow passing from the inlet towards the vacuum source.

9. The surgical device system of claim 1, further comprising an illumination source disposed at the distal end of the surgical tool assembly.

10. The surgical device system of claim 1, further comprising a control switch configured to receive an activation signal from a receiver selected from the group consisting of radio, WIFI, and infrared.

11. An attachment for use with a surgical device having a body with a distal end and a proximal end, the attachment disposed in fluid communication with a vacuum source, the attachment comprising:
   a body having a distal end, and a proximal end;
   a fluid intake port disposed on the body of the attachment and disposed adjacent to the distal end of the surgical device;
   a blower port disposed on the body of the attachment and disposed adjacent to the distal end of the surgical device;
   a vacuum port disposed on the body of the attachment and configured for fluid communication with the vacuum source;
   a blower disposed in fluid communication with the blower port, the blower operable to cause a fluid flow out of the blower port toward the surgical device and the fluid intake port;
   a canister having an inlet and an outlet configured for fluid communication with the vacuum source and the fluid intake port, the canister configured to removably attach to the attachment; and,
   a filter cartridge having an inlet and an outlet configured for fluid communication with the vacuum source, the fluid intake port, and the canister, wherein the canister is operable to cause liquids to be captured within the canister and allows other fluids to pass to the filter cartridge.

12. The attachment of claim 11, further comprising an RFID reader for reading an RFID tag on the filter cartridge.

13. The attachment of claim 11, further comprising an RFID writer disposed on the body of the tool assembly for writing filter usage data to a writeable RFID tag on the disposable filter.

14. The attachment of claim 11, further comprising a moisture wick for absorbing moisture from a flow passing from the inlet towards the vacuum source.

15. The attachment of claim 11, further comprising an illumination source disposed at the distal end of the tool assembly.

16. A method for vacuum suction for a surgical device, the surgical device having a body with a distal end and a proximal end, the surgical device generating aerosol in a surgical environment, the method comprising:
   providing an attachment with a body having a distal end, and a proximal end;
   providing a fluid intake port disposed on the body of the attachment and disposed adjacent to the distal end of the surgical device;
   providing a blower port disposed on the body of the attachment and disposed adjacent to the the distal end of the surgical device;
   providing a vacuum port disposed on the body of the attachment and configured for fluid communication with the vacuum source;
   providing a blower disposed in fluid communication with the blower port, the blower operable to cause a fluid flow out of the blower port toward the surgical device and the fluid intake port;
   providing a canister having an inlet and an outlet configured for fluid communication with the vacuum source and the fluid intake port, the canister configured to removably attach to the attachment; and,
   providing a filter cartridge having an inlet and an outlet configured for fluid communication with the vacuum source, the fluid intake port, and the canister, wherein the canister is operable to cause liquids to be captured within the canister and allows other fluids to pass to the filter cartridge;
   installing the attachment on the surgical device;
   activating the surgical device;
   activating the vacuum source and the blower to provide vacuum for removing the aerosol from the surgical environment.

* * * * *